United States Patent [19]
Diei et al.

[11] Patent Number: 5,298,889
[45] Date of Patent: Mar. 29, 1994

[54] METAL CUTTING MACHINE TOOL BREAK DETECTION

[75] Inventors: Edward N. Diei, Cincinnati; Jerry H. Carmichael, West Chester, both of Ohio; Steven R. Hayashi, Schenectady, N.Y.

[73] Assignee: General Electric Company, Cincinnati, Ohio

[21] Appl. No.: 895,080

[22] Filed: Jun. 8, 1992

[51] Int. Cl.[5] .......................................... G08B 21/00
[52] U.S. Cl. ........................................ 340/680; 73/104; 73/660; 340/683; 364/474.17
[58] Field of Search ................... 340/680, 683; 73/104, 73/660; 364/508, 474.17

[56] References Cited
U.S. PATENT DOCUMENTS

| | | | |
|---|---|---|---|
| 3,548,648 | 12/1970 | Weichbrodt et al. | 73/104 |
| 4,120,196 | 10/1978 | Hamilton et al. | 73/104 |
| 4,220,995 | 9/1980 | Shoda | 364/508 |
| 4,558,311 | 12/1985 | Forsgren et al. | 340/680 |
| 4,559,600 | 12/1985 | Rao | 364/474.17 |
| 4,615,216 | 10/1986 | Vykoupil | 73/593 |
| 4,636,779 | 1/1987 | Thomas et al. | 340/680 |
| 4,636,780 | 1/1987 | Thomas et al. | 340/680 |
| 4,642,617 | 2/1987 | Thomas et al. | 340/680 |
| 4,707,688 | 11/1987 | Thomas | 340/680 |
| 4,744,242 | 5/1988 | Anderson et al. | 73/104 |
| 4,831,365 | 5/1989 | Thomas et al. | 340/680 |
| 4,918,427 | 4/1990 | Thomas et al. | 340/680 |
| 4,942,387 | 7/1990 | Thomas | 340/683 |
| 4,989,159 | 1/1991 | Liszka et al. | 364/508 |

Primary Examiner—Thomas Mullen
Attorney, Agent, or Firm—Jerome C. Squillaro; Charles L. Moore, Jr.

[57] ABSTRACT

A composite low frequency high frequency electrical signal from a metal cutting tool in a metal cutting operation is processed through separate high frequency and low frequency systems and the resulting signals digitized and combined for analysis of a tool break event.

18 Claims, 3 Drawing Sheets

METAL CUTTING MACHINE TOOL BREAK DETECTION

BACKGROUND OF THE INVENTION

This invention relates to tool break detection of metal cutting machine tools, and more particularly to an improved electronic system and method which more clearly isolates a tool break generated electrical signal or signal change from other interfering electrical signals and changes encountered in usual metal cutting operations.

Prior tool break detection systems have utilized an interruption in a certain vibration generated electrical signal, taken from an operating cutting tool, to identify tool breakage. For example, a vibration generated electrical signal, as taken from an operating metal cutting tool, may be appropriately processed and displayed to show a characteristic spike or signal interruption upon tool breakage. Other systems may employ both low frequency and high frequency signals (as well as their mean values) in break detection analysis.

In metal cutting processes and procedures, an electrical signal which is representative of the cutting process and produced for example, by the use of an accelerometer attached to the machine, may be deleteriously affected by extraneous signals generated from normal and abnormal changes in the cutting process such as changes in the tool feed and speed, metal chip buildup, high frequency chatter, etc. These conditions may be components of the electrical signal to be processed and analyzed, and may tend to reduce the clarity and distinguishing characteristics of a spike interruption correlated to tool breakage. For example, low frequency and high frequency signals both contain important information about the cutting process and tool break events. A low frequency signal measures large scale vibrations and may be less sensitive to certain higher frequency components emanating from, for example, metal chips and their distribution as well as from tool break related phenomena. Analysis of one of such signals may lead to errors because the one signal may not contain critical tool break information. Analysis of both low frequency and high frequency signals requires more complex determinations to appraise and dismiss random noise and occurrences which may give erroneous indications of tool breakage.

OBJECTS OF THE INVENTION

Accordingly, it is an object of this invention to provide an improved tool break detection system which more clearly isolates a tool break signal from other signals generated during a metal cutting process.

It is another object of this invention to provide an improved tool break electrical signal isolation system utilizing an integral combination of a cutting tool generated UE (ultrasonic emission) electrical signal and a low frequency, LF, electrical signal.

It is a further object of this invention to provide an improved tool break detection system utilizing a combination electrical signal comprising a cutting tool generated UE signal and a LF electrical signal which are integrally combined in a composite signal which is divided and processed through separate high frequency and low frequency signal processing paths or channels to provide a signal upon a tool break occurrence.

SUMMARY OF THE INVENTION

A metal cutting machine tool break detection system utilizes a composite electrical signal of an ultrasonic emission electrical signal and a low frequency electrical signal, both taken from cutting tool operation, as a unitary and integral signal which is processed through separate high frequency and low frequency signal processing paths or channels to distinguish between signals from actual tool breaks and signals from usual changes in tool operation during the cutting process (feed, speed, direction, etc.). The output signals from the separate processing channels are combined with a gain signal for further processing to determine tool breakage.

This invention will be better understood when taken in connection with the following drawing and description.

DESCRIPTION OF A PREFERRED EMBODIMENT

Figure 1:
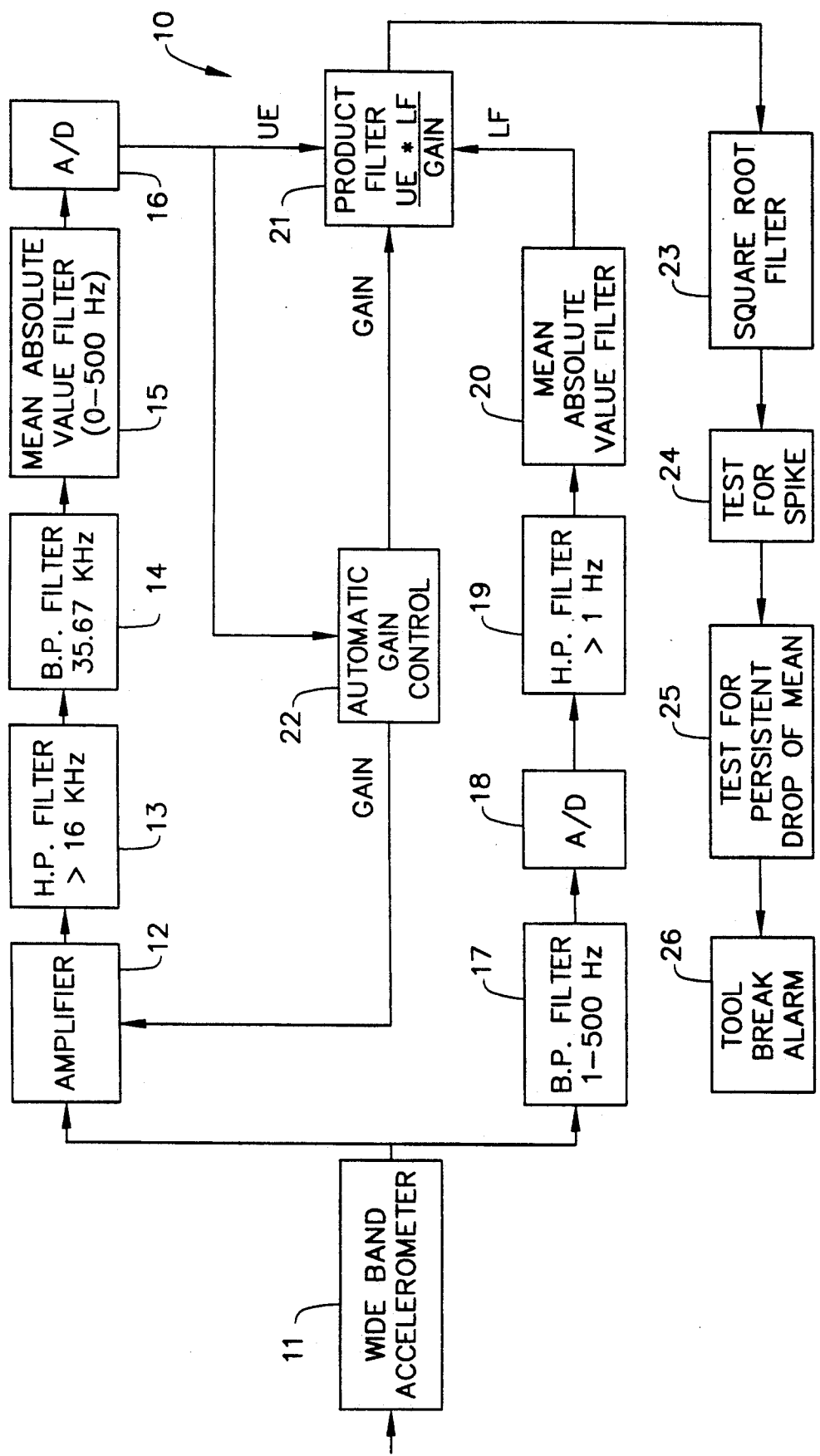
FIG. 1 is a block diagram flow chart of interconnected components representing the detection system of this invention.

Referring now to FIG. 1, detection system 10 utilizes a composite electrical signal taken from a metal cutting tool during its operation. For example, a wideband accelerometer 11 is attached to a machine tool usually at the spindle in which a rotary cutter tool is mounted or the workpiece or part holding fixture. The accelerometer 11 is a vibration sensor which generates an electrical signal representing vibrations originating from the tool/workpiece interface. The electrical signal from accelerometer 11 is divided and processed through separate parallel high frequency and low frequency processing channels and then combined with a gain signal for final analysis. In the high frequency channel, the electrical signal output from accelerometer 11 is passed into a variable gain amplifier 12 and then subjected to a series of filters including a high pass filter 13 (>16 KHz) and a band pass filter 14 (35-67 KHz). The output signal from filter 14 is passed into a MAV filter 15 (Mean Absolute Value, 0-500 Hz) which converts the signal to an energy signal. The output signal from MAV filter 15 is passed to a converter 16 which converts the passing signal from an analog signal to a digital signal with the output signal from MAV filter 16 being the UE signal of system 10.

The low frequency channel of system 10 takes its branch signal from accelerometer 11 and passes it through a band pass filter 17 (1-500 Hz) with the output signal from filter 17 being sampled and converted from analog to digital form in converter 18. The output signal from converter 18 is passed to a high pass filter 19 (>1 Hz) to remove any d.c. drift, and then passed to MAV filter 20 for conversion to an energy signal, mean-absolute-value, which is the LF (low frequency) signal of system 10.

The UE signal from analog to digital converter 16 and the LF signal from MAV filter 20 are passed to product filter 21. At the same time, a branch of the UE signal is passed to an automatic gain control unit 22 which is also connected to amplifier 12 in which gain was added to the signal from accelerometer 11. The output signal from unit 22 provides a signal indicative of the gain applied to the UE signal in its channel. This gain signal together with the UE and LF signals are passed into product filter 21 which calculates the product $$\frac{UE*LF}{GAIN}$$

and, in order to maintain the same order of magnitude in the dynamic range, the square root of the composite signal from filter 21 is calculated in filter 23 and the resultant signal is passed to a transient detector 24.

Detector 24 is programmed to detect a signal spike, e.g., any abrupt transient increase or decrease in the noted resultant signal, and, upon such an occurrence the persistence tester 25 includes appropriate logic circuitry to measure the length of time over which the transient persists. Within a predetermined and adjustable range in tester 25, a short term transient is rejected. However, if the transient time is more than a predetermined length, the signal is treated as a tool break signal which initiates an appropriate response signal or alarm in signal system 26. Such a response signal may be an audio visual alarm signal, or an appropriate signal interjected into an overall machine monitoring system. Such a signal may be a control signal for effecting a change in the tool cutting machine operation. Persistence sensor 25 is made user adjustable so that an alarm is not sounded for spurious signals caused by variations in the cutting process other than tool breakage, for example, initial cuts on a rough surface from prior casting or forging operations and run-out on initial cuts. Such abrupt transitions unfortunately have many of the signal characteristics associated with tool break. These and other occurrences may be short lived or repetitive and accordingly persistence detector 25 is adjusted to provide for a confirmation time period for such occurrences before an alarm is sounded. For example, the confirmation period can be set for a sufficient period of time to prevent a run-out false alarm at the slowest tool spindle speed to be used in most or any planned cut. The confirmation period may be shortened to reduce the probability of missing actual tool breaks when cutting conditions do not involve runout or when high tool spindle speeds are to be employed.

Figure 2:
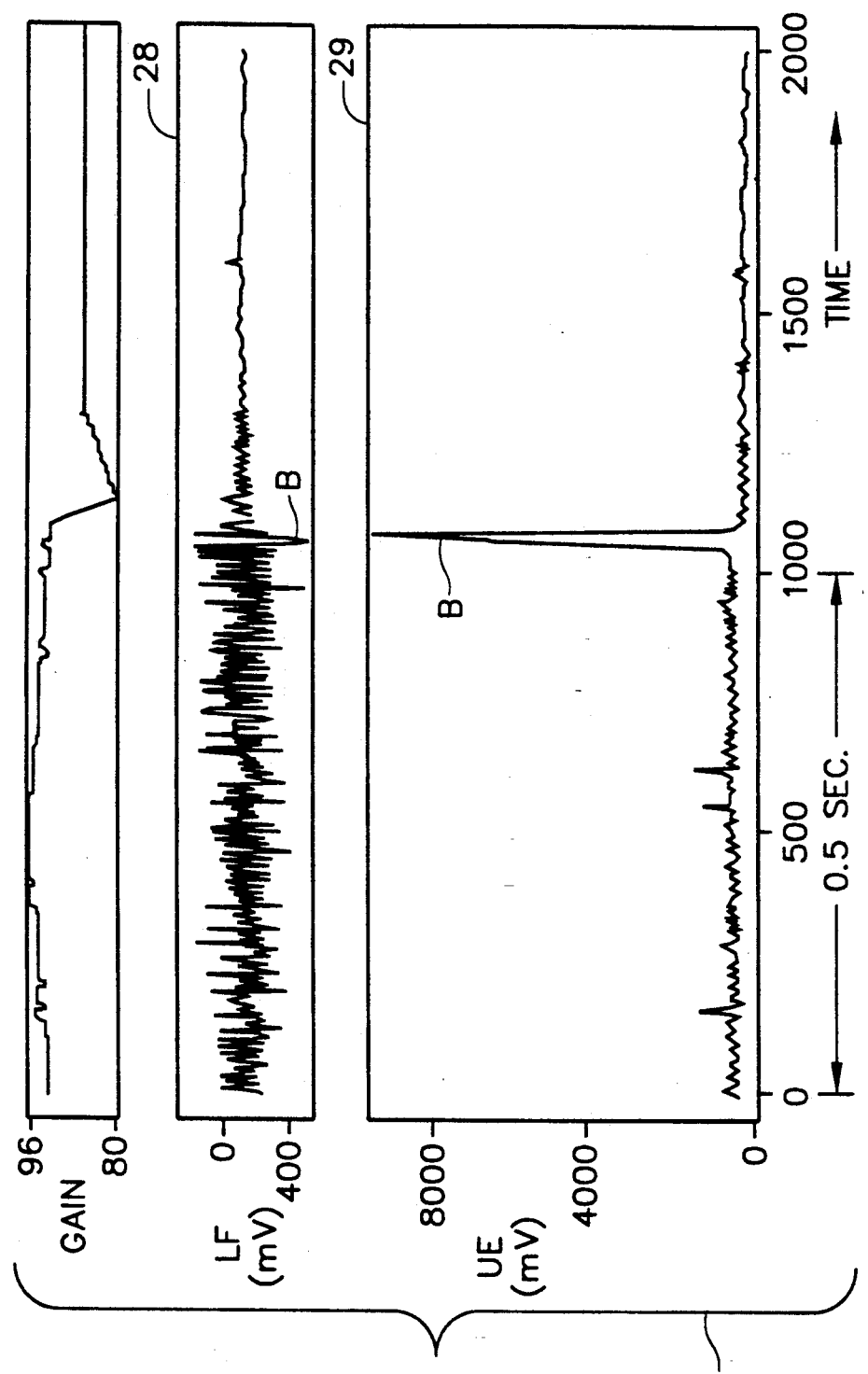
FIG. 2 is a graphical representation or readout of a tool break occurrence resulting from a practice of the system of FIG. 1.

One example of a practice of this invention in processing a tool signal through the system of FIG. 1 is illustrated in FIG. 2.

Referring now to FIG. 2, tool signal composite representation 27 illustrates a one second segment of a tool signal encompassing a tool break event. In this instance the cutting tool was a four flute 0.75 inch carbide end mill which was utilized in cutting a stainless steel alloy at 1400 R.P.M. The "break" spike or signal B is shown for both the low frequency LF and ultrasonic emission UE frequency signals 28 and 29, respectively.

Figure 3:
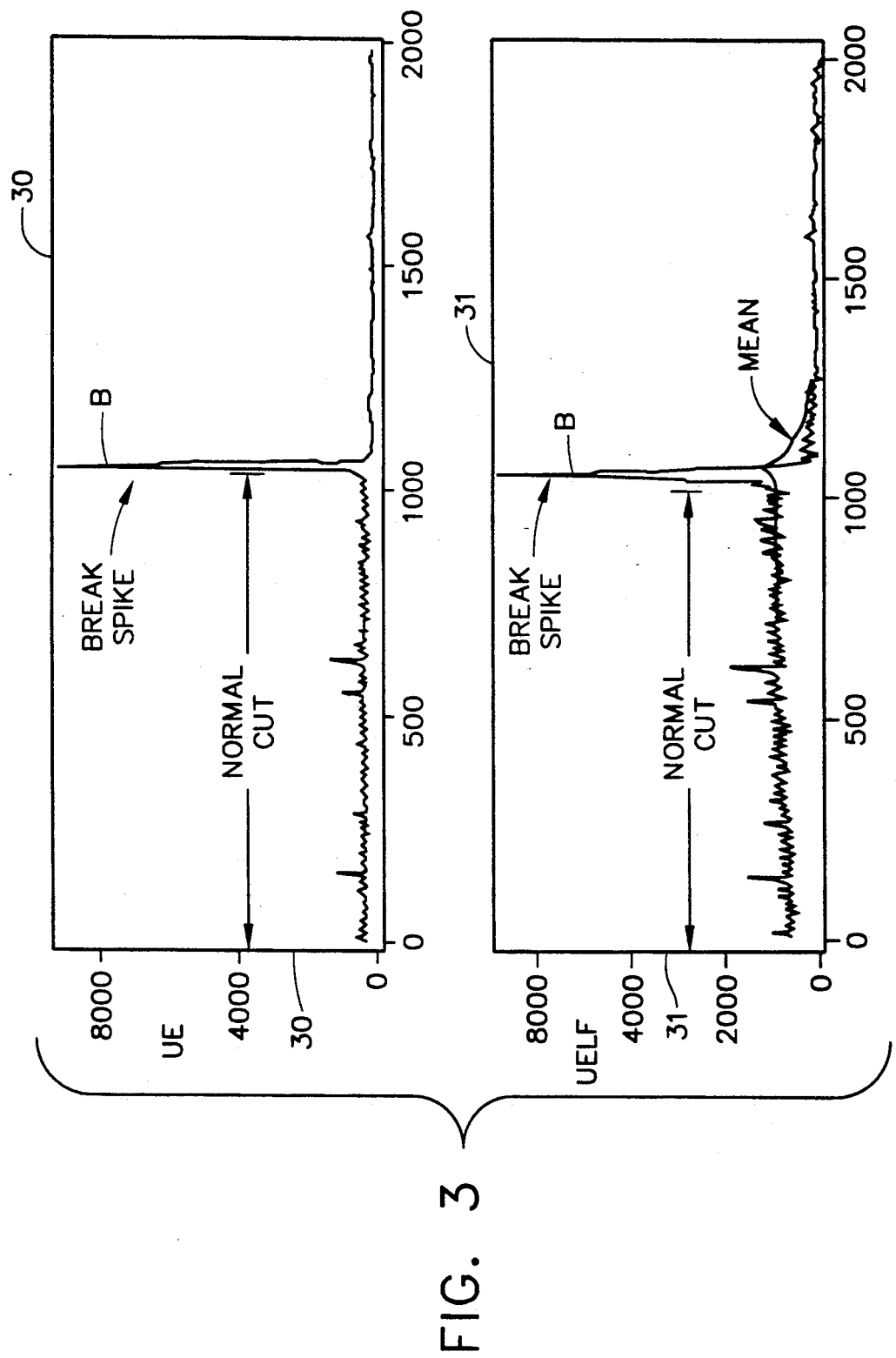
FIG. 3 is a graphical comparison of different electrical signals showing the same tool break event.

A comparison of a break signal involving only a UE signal, as compared to the break signal of a composite signal UE-LF of the present invention is illustrated in FIG. 3.

Referring now to FIG. 3, the signal representations 30 and 31 correspond to the segment 27 of FIG. 2. In FIG. 3, signal 30 of the UE signal alone illustrates a tool break event B while signal 31 illustrates the same tool break event represented by the composite UE-LF signal of the present invention. The composite signal minimizes the effects of random noise spikes, and most importantly, amplifies a drop in mean signal level after the tool break event, all of which improve the separation between "break" and non-break signals. A most significant feature in FIG. 3 is that the ratio of mean before the spike to the mean after the spike, for UE-LF is about 13.6 within the verification time or region compared to a value of about 7.0 for UE alone. This represents a significant improvement in one of the critical parameters (the noted ratio) utilized for tool break detectors.

This invention discloses a metal cutting tool break detection system which utilizes a composite vibration generated electrical signal with both low frequency and high frequency components. Both signals individually contain important information concerning the metal cutting process as well as tool breakage. The combined signal is passed through parallel high frequency and low frequency processing paths, the signals of each path being subsequently digitized combined and analyzed for tool breakage characteristics. The combined signal improves the quantitative separation between tool break and non-tool break events for more improved and positive determination of a tool break event.

For a more specific description, this invention encompasses a general signal processing system which employs a composite vibration generated electrical signal from a metal cutting tool during its cutting process. This composite signal, having major low frequency and high frequency components, is passed through separate parallel processing filtering paths to provide, from one path a high pass band pass filtered signal having its MAV converted from analog to digital as a UE signal. From the low frequency path the composite signal is appropriately band pass filtered, converted to a digitized signal which is high pass filtered, then converted to an energy signal in a MAV filter to provide a LF signal from the LF path. The LF and UE signals are combined with a gain signal and processed to determine significant tool break indication or isolate any signal characteristic indicative of a tool break event. Processing of the UE, LF, and gain signals includes passing them to a product filter to calculate the product $$\frac{UE*LF}{GAIN}$$

and then passing the product to a square root filter and to a test unit which monitors the mean value of the signal to sense a persistent change in the mean value according to a predetermined time span which, if exceeded, generates a warning or alarm, signal.

U.S. Pat. No. 4,636,780 - Thomas et al, Jan. 13, 1987, assigned to the same assignee as the present invention, discloses digital circuitry utilized to analyze a digital signal to discern a cutting tool break event.

While this invention has been disclosed and described with respect to a preferred embodiment, it will be understood by those skilled in the art that various changes and modifications may be made without departing from the spirit and scope of the invention.

What is claimed:

1. A method for determining a metal cutting tool break event during a cutting process, comprising the steps of:

(a) sensing vibrations during the cutting process;

(b) generating a composite electrical vibration signal having a low frequency component and a high frequency component from said sensed vibrations;

(c) processing the composite signal through a high frequency processing path and through a low frequency processing path;

(d) deriving separate digitized UE (ultrasonic emission) and gain signals from the high frequency processing path;

(e) deriving a digitized LF (low frequency) signal from the low frequency processing path;

(f) passing the UE, gain, and LF digitized signals through a product filter which outputs a signal representing the product:

$$\frac{UE*LF}{GAIN};$$

and (g) processing the $$\frac{UE*LF}{GAIN}$$

output signal to determine whether a tool break event has occurred.

2. The invention as recited in claim 1, further comprising the step of passing the output signal through a square root filter which outputs a square root value signal.

3. The invention as recited in claim 2, further comprising the step of passing the square root value signal through a transient signal detector to determine whether a tool breakage event has occurred.

4. The invention as recited in claim 3, further comprising the step of passing a signal from the transient detector through a signal mean tester to monitor the mean value of the signal passed by the transient detector and to determine whether any shift of the mean value persists for a predetermined time.

5. The invention as recited in claim 4, further comprising the step of generating a response signal when a shift in the mean value persists for the predetermined time.

6. A method for determining a tool break event, comprising the steps of:

(a) sensing vibrations during a metal cutting process;

(b) generating a composite electrical vibration signal having a low frequency component and a high frequency component from said sensed vibrations;

(c) processing the composite signal through a high frequency signal processing path and through a low frequency signal processing path;

(d) deriving separate digitized UE (ultrasonic emission) and gain signals from the high frequency processing path;

(e) deriving a digitized LF (low frequency) signal from the low frequency processing path;

(f) passing the UE, gain, and LF digitized signals through a product filter which outputs a signal representing the product:

$$\frac{UE*LF}{GAIN};$$

(g) passing the output signal from the product filter through a square root filter which outputs a square root value signal;

(h) passing the square root value signal through a transient signal detector which detects abrupt changes in the electrical signal passing therethrough and provides an output signal indicative thereof;

(i) passing the transient detector output signal through a signal mean tester component to monitor the mean value of the transient detector output signal and to determine whether any shift of the mean value persists for a predetermined period of time; and (j) initiating a response signal indicative of tool breakage when a shift in the mean value persists for the predetermined period of time.

7. The invention as recited in claim 6, wherein said low frequency component is in the range of from about 0 to about 500 Hz.

8. The invention as recited in claim 6, wherein said high frequency component is in the range from about 20 to 80 KHz.

9. The invention as recited in claim 6, wherein the high frequency path includes series arranged components comprising a gain control, high pass filter, band pass filter, MAV (mean-absolute-value) filter, and an A-D converter having an output signal which is the UE (ultrasonic emission) signal.

10. The invention as recited in claim 6, wherein said low frequency path includes series arranged components comprising a band pass filter, an A-D converter, a high pass filter, and a MAV (means-absolute-value) filter, an output signal from said MAV filter representing the LF signal.

11. A device for detecting a tool break in a cutting machine tool, comprising:

a high frequency processing path to provide an ultrasonic emission (UE) signal and a gain signal from a vibration signal representative of vibrations sensed from the cutting machine tool during a cutting process;

a low frequency processing path to provide a low frequency (LF) signal from the vibration signal;

a product filter to provide a composite output signal which is a function of the UE signal, the gain signal and the LF signal;

a transient detector to detect a transient in the composite output signal; and means for generating a response signal if the transient persists for a predetermined time period.

12. The device of claim 11, further comprising a square root filter interconnected between said product filter and said transient detector to provide a resulting signal which is a square root of the composite output signal.

13. The device of claim 11, wherein said response signal generating means is adjustable to change the predetermined time period so that a response signal is only generated in response to a tool breakage and not in response to a spurious signal caused by a variation in the cutting process.

14. The device of claim 13, wherein said response signal generating means comprises an adjustable persistence sensor to measure a duration of time over which the transient occurs.

15. The device of claim 13, wherein the response signal is at least one of an audio/visual alarm signal for giving a perceivable indication of tool breakage and a control signal for causing a change in operation of the cutting machine tool.

16. The device of claim 11, wherein said low frequency processing path is connected in parallel with said high frequency processing path between an accelerometer, which generates the vibration signal, and said product filter.

17. The device of claim 16, wherein said high frequency processing path comprises:
an amplifier for receiving a portion of the vibration signal from the accelerometer and for generating an amplifier vibration signal;
a high pass filter electrically connected to said amplifier for receiving the amplified vibration signal;
a band pass filter electrically connected to said high pass filter for receiving an output signal therefrom;
a mean absolute value (MAV) filter electrically connected to said band pass filter to receive an output signal therefrom and to convert the band pass filter output signal to an energy signal;
an analog to digital converter electrically connected to the MAV filter to convert the energy signal to the UE signal, an output of said analog to digital converter being electrically connected to said product filter; and
an automatic gain control electrically connected to the output of said analog to digital converter and outputs of said automatic gain control being respectively electrically connected to said amplifier and to said product filter.

18. The device of claim 16, wherein said low frequency processing path comprises:
a band pass filter for receiving a portion of the vibration signal from the accelerometer and for generating a filtered output signal;
an analog to digital converter electrically connected to said band pass filter to convert the filtered output signal to a digital signal;
a high pass filter electrically connected to said analog to digital converter to remove any d.c. drift from the digital signal; and
a mean absolute value (MAV) filter electrically connected to said high pass filter to output the low frequency (LF) signal, said MAV filter being electrically connected to said product filter.

* * * * *